(12) United States Patent
Dietrich et al.

(10) Patent No.: US 11,623,947 B2
(45) Date of Patent: Apr. 11, 2023

(54) COLLAGEN POWDER

(71) Applicant: Innocoll Pharmaceuticals Limited, Athlone (IE)

(72) Inventors: Alexandra Dietrich, Saal (DE); Michael Myers, Ashburn, VA (US); Stefan Schneid, Saal (DE)

(73) Assignee: Innocoll Pharmaceuticals Limited, Athlone (IE)

( * ) Notice: Subject to any disclaimer, the term of this patent is extended or adjusted under 35 U.S.C. 154(b) by 0 days.

(21) Appl. No.: 13/858,382

(22) Filed: Apr. 8, 2013

(65) Prior Publication Data

US 2014/0303347 A1 Oct. 9, 2014

(51) Int. Cl.
*A61K 8/65* (2006.01)
*C07K 14/78* (2006.01)

(52) U.S. Cl.
CPC .................................. *C07K 14/78* (2013.01)

(58) Field of Classification Search
CPC ...... A61K 38/014; A61K 35/35; A61K 8/022; A61K 8/65
See application file for complete search history.

(56) References Cited

U.S. PATENT DOCUMENTS

| | | | |
|---|---|---|---|
| 4,273,705 A * | 6/1981 | Kato | A61L 15/325 106/157.3 |
| 4,273,750 A * | 6/1981 | Hollett, Jr. | B01D 53/508 422/176 |
| 4,412,947 A | 11/1983 | Cioca | |
| 5,138,030 A * | 8/1992 | Pachence | 530/356 |
| 5,196,185 A | 3/1993 | Silver et al. | |
| 5,219,576 A * | 6/1993 | Chu | A61K 38/39 128/DIG. 8 |
| 6,613,348 B1 * | 9/2003 | Jain | A61L 15/325 424/402 |
| 8,951,314 B2 * | 2/2015 | Leininger | C10J 3/506 48/62 R |
| 2009/0246280 A1 * | 10/2009 | Yamashita | 424/486 |
| 2010/0254900 A1 * | 10/2010 | Campbell | C12N 5/0068 424/1.65 |
| 2013/0190479 A1 * | 7/2013 | Tanaka | A61K 8/022 530/356 |
| 2013/0199993 A1 * | 8/2013 | Wong | B01D 39/1676 210/500.1 |
| 2013/0210713 A1 * | 8/2013 | Ten Kate et al. | 514/4.8 |
| 2015/0004414 A1 * | 1/2015 | Ogura | A61P 43/00 428/401 |

FOREIGN PATENT DOCUMENTS

| | | |
|---|---|---|
| GB | 2147299 | 5/1985 |
| JP | S 58212447 A | 12/1983 |
| JP | H 03169900 A | 7/1991 |
| WO | 2011139228 | 11/2011 |
| WO | WO 2012/015055 A1 | 2/2012 |

OTHER PUBLICATIONS

European Application No. EP 13162799.4, Extended European Search Report dated Jul. 31, 2013, 10 pages.
PCT Application No. PCT/EP2014/057091, International Search Report and Written Opinion dated May 19, 2014, 10 pages.
PCT Application No. PCT/EP2014/057091, International Preliminary Report on Patentability dated Oct. 13, 2015, 8 pages.

* cited by examiner

*Primary Examiner* — Karen Cochrane Carlson
(74) *Attorney, Agent, or Firm* — Morgan, Lewis & Bockius LLP

(57) ABSTRACT

There is a need to provide a collagen powder having desirable product characteristics, such as high fluid absorption capacity, while also having processing characteristics that allow commercial manufacturing and handling of the collagen powder. The present invention relates to a collagen powder, a method of manufacture thereof, and uses thereof. In particular, the present invention relates to a process for preparing a collagen powder, the process comprising the steps of providing a collagen source; adjusting the concentration of the collagen source; adjusting the pH of the collagen source; freezing the collagen source; dehydrating the frozen collagen; and degrading the dehydrated collagen to a powder.

26 Claims, 1 Drawing Sheet

COLLAGEN POWDER

FIELD OF THE INVENTION

The present invention relates to a collagen powder, a method of manufacture thereof, and uses thereof.

BACKGROUND TO THE INVENTION

Processes for the preparation of collagen-based powders for use in human and veterinary medicine are well known in the art. One important performance characteristic of collagen powders is the ability to absorb fluids, such as blood and/or wound exudate. Given that collagen powders often show low density, optimized processing characteristics are also of paramount importance.

Commonly, the collagen used for subsequent preparation of the collagen-based powders is first isolated by extraction from mammalian hide or tendon, purified, enzymatically-treated to remove non-helical telopeptides, partially solubilised with acid, and finally precipitated by increasing the pH to provide a source of purified, fibrillar collagen. Once isolated, the collagen source may be further processed for the manufacture of collagen-based materials immediately, or is otherwise stored while waiting further processing. For storage convenience at commercial scale, the collagen source is normally concentrated by removal of water using centrifugation to reduce bulk and thereby create a wet mass. The wet mass must be stored frozen to preserve the collagen and prevent bacterial growth. When needed for manufacture of collagen-based powders, the frozen collagen wet mass is typically thawed and redispersed. Whether the isolated collagen is used immediately or frozen and thawed as a wet mass, the collagen source is generally viscous and difficult to process at commercial scale into collagen-based powders.

It is known to prepare collagen powders by milling pre-formed collagen sponge products. Disadvantageously, this known method results in collagen powders having low density. Moreover, a large number of collagen sponges must be formed in order to prepare a sufficient amount of collagen powder, which makes the collagen powder preparation process inefficient, particularly given that the amount of water that needs to be removed during the preparation process can be approximately 200-fold greater than the equivalent dry mass of the collagen source. In addition, the resulting collagen powder is difficult to further process because it exhibits undesirable processing characteristics, such as poor flow behaviour and high electrostatic charge properties. These material properties also lead to difficulties in the application of the resulting collagen powder, for example, for use in woundcare or implantation. Due to the low density of the resulting collagen powder, it can easily be blown away by minor air movements and adheres to surfaces, which can complicate placement of the collagen powder at the site of application.

There is a need to provide a collagen powder having desirable product characteristics, such as high fluid absorption capacity, while also having processing characteristics that allow commercial manufacturing and handling of the collagen powder.

SUMMARY OF THE INVENTION

According to a first aspect of the present invention, there is provided a process for preparing a collagen powder, the process comprising the steps of:

(a) providing a collagen source;
(b) adjusting the collagen source to a concentration of 1.5-4.0%;
(c) adjusting the collagen source to a pH of 3.5-5.0;
(d) freezing the collagen source;
(e) dehydrating the frozen collagen; and
(f) degrading the dehydrated collagen to a powder.

Optionally, the concentration-adjusting step (b) is performed prior to the pH-adjusting step (c). Alternatively, the pH-adjusting step (c) is performed prior to the concentration-adjusting step (b). Further alternatively, the concentration-adjusting step (b) and the pH-adjusting step (c) are performed simultaneously.

Optionally, the collagen source in the providing step (a) is fibrillar collagen. Further optionally, the collagen source in the providing step (a) is selected from Type I collagen, Type II collagen, Type III collagen, and a mixture thereof. Still further optionally, the collagen source in the providing step (a) is Type I collagen.

Optionally, the collagen source in the providing step (a) has a collagen concentration of greater than 4.0%. Further optionally, the collagen source in the providing step (a) has a collagen concentration of greater than 15.0%. Still further optionally, the collagen source in the providing step (a) has a collagen concentration of greater than 30.0%.

Optionally, the collagen source in the providing step (a) has a pH greater than 5.0. Further optionally, the collagen source in the providing step (a) has a collagen concentration of 7.0. Still further optionally, the collagen source in the providing step (a) has a collagen concentration of greater than 7.0.

Optionally, the process comprises the additional step of mechanically degrading the collagen source prior to the freezing step (d). Further optionally, the process comprises the additional step of homogenising the collagen source prior to the freezing step (d). Still further optionally, the process comprises the additional step of shear mixing the collagen source prior to the freezing step (d).

Optionally, the additional mechanical degrading step is conducted after the concentration-adjusting step (b) and/or the pH-adjusting step (c); and prior to the freezing step (d).

Optionally, the additional mechanical degrading step is conducted for a period of more than 5 seconds. Further optionally, the additional mechanical degrading step is conducted for a period of 5-900 seconds. Still further optionally, the additional mechanical degrading step is conducted for a period of 5-900 seconds until a homogenous collagen dispersion is formed.

Optionally, the concentration-adjusting step (b) comprises introducing a fluid to the collagen source. Further optionally, the concentration-adjusting step (b) comprises introducing an aqueous fluid to the collagen source. Still further optionally, concentration-adjusting step (b) comprises introducing water, optionally purified water, to the collagen source.

Optionally, the collagen source is adjusted to an equivalent concentration of 1.5-4.0% (w/w) dry collagen. Further optionally, the collagen source is adjusted to an equivalent concentration of 2.0-3.5% (w/w) dry collagen.

Optionally, the process comprises the step (c) of adjusting the collagen source to a pH of less than 4.5. Further optionally, the process comprises the step (c) of adjusting the collagen source to a pH of 3.8-4.3. Still further optionally, the process comprises the step (c) of adjusting the collagen source to a pH of 4.0.

Optionally, the pH-adjusting step (c) comprises introducing an acid to the collagen source. Further optionally, the pH-adjusting step (c) comprises introducing an acid solution to the collagen source. Still further optionally, the pH-adjusting step (c) comprises introducing an aqueous acid solution to the collagen source.

Optionally, the pH-adjusting step (c) comprises introducing a carboxylic acid to the collagen source. Further optionally, the pH-adjusting step (c) comprises introducing a carboxylic acid solution to the collagen source. Still further optionally, the pH-adjusting step (c) comprises introducing an aqueous carboxylic acid solution to the collagen source.

Optionally, the pH-adjusting step (c) comprises introducing a sulfonic acid to the collagen source. Further optionally, the pH-adjusting step (c) comprises introducing a sulfonic acid solution to the collagen source. Still further optionally, the pH-adjusting step (c) comprises introducing an aqueous sulfonic acid solution to the collagen source.

Optionally, the pH-adjusting step (c) comprises introducing a mineral acid to the collagen source. Further optionally, the pH-adjusting step (c) comprises introducing a mineral acid solution to the collagen source. Still further optionally, the pH-adjusting step (c) comprises introducing an aqueous mineral acid solution to the collagen source.

Optionally, the pH-adjusting step (c) comprises introducing acetic acid to the collagen source. Further optionally, the pH-adjusting step (c) comprises introducing an acetic acid solution to the collagen source. Still further optionally, the pH-adjusting step (c) comprises introducing an aqueous acetic acid solution to the collagen source.

Optionally, pH—the adjusting step (c) comprises introducing anhydrous acetic acid to the collagen source.

Optionally, the concentration-adjusting step (b) and the pH-adjusting step (c) can be conducted simultaneously by introducing an acid solution, optionally an aqueous acid solution, to the collagen source.

Optionally, the concentration-adjusting step (b) and the pH-adjusting step (c) can be conducted simultaneously by introducing an acetic acid solution, optionally an aqueous acetic acid solution, to the collagen source.

Optionally, the concentration-adjusting step (b) is conducted for a period of not less than 0.5 hours. Further optionally, the concentration-adjusting step (b) is conducted for a period of 0.5 hours.

Optionally, the pH-adjusting step (c) is conducted for a period of 1-180 minutes.

Optionally, the concentration-adjusting step (b) and the pH-adjusting step (c) are conducted simultaneously for a period of more than 1 minute. Further optionally, the concentration-adjusting step (b) and the pH-adjusting step (c) are conducted simultaneously for a period of 1-180 minutes.

Optionally, the freezing step (d) comprises freezing to a temperature of about −33° C. to about −42° C. Further optionally, the freezing step (d) comprises freezing to a temperature of about −38° C. Still further optionally, the freezing step (d) comprises freezing at a rate of about 0.3° C. to about 1.5° C. per minute, optionally a rate of about 0.5° C. per minute.

Optionally, the dehydrating step (e) comprises removing the aqueous phase. Further optionally, the dehydrating step (e) comprises removing the aqueous phase by reducing the pressure. Still further optionally, the dehydrating step (e) comprises removing the aqueous phase by reducing the pressure to about 0.05 to about 1 mbar. Still further optionally, the dehydrating step (e) comprises removing the aqueous phase by applying at least a partial vacuum, optionally by applying a vacuum.

Optionally or additionally, the dehydrating step (e) comprises increasing the temperature. Further optionally or additionally, the dehydrating step (e) comprises increasing the temperature under vacuum or partial vacuum. Still further optionally or additionally, the dehydrating step (e) comprises increasing the temperature to at least +30° C. Still further optionally or additionally, the dehydrating step (e) comprises increasing the temperature to at least +30° C. under vacuum or partial vacuum. Still further optionally or additionally, the dehydrating step (e) comprises increasing the temperature to at least +40° C. Still further optionally or additionally, the dehydrating step (e) comprises increasing the temperature to at least +40° C. under vacuum or partial vacuum.

Optionally or additionally, the dehydrating step (e) comprises increasing the temperature to about +30° C. at a rate of about 0.3° C. to about 1.5° C. per minute, further optionally at a rate of about 0.5° C. per minute. Further optionally or additionally, the dehydrating step (e) comprises increasing the temperature of the collagen to about +30° C. at a rate of about 0.3° C. to about 1.5° C. per minute, further optionally at a rate of about 0.5° C. per minute, under vacuum or partial vacuum.

Optionally or additionally, the dehydrating step (e) comprises increasing the temperature to about +40° C. at a rate of about 0.3° C. to about 1.5° C. per minute, further optionally at a rate of about 0.5° C. per minute. Further optionally or additionally, the dehydrating step (e) comprises increasing the temperature of the collagen to about +40° C. at a rate of about 0.3° C. to about 1.5° C. per minute, further optionally at a rate of about 0.5° C. per minute, under vacuum or partial vacuum.

Optionally, the dehydrating step (e) comprises at least one equilibrating step.

Optionally, the at least one equilibrating step comprises maintaining the temperature at a constant temperature, sufficient to allow the frozen collagen to reach a desired temperature. Further optionally, the at least one equilibrating step comprises maintaining the temperature at a constant temperature for a sufficient period of time to allow the frozen collagen to reach a desired temperature. Still further optionally, the at least one equilibrating step comprises maintaining the temperature at a constant temperature for at least 10 mins, optionally at least 20 mins, further optionally at least 30 mins, still further optionally at least 45 mins, still further optionally at least 60 mins; to allow the frozen collagen to reach a desired temperature.

Optionally, the at least one equilibrating step is conducted when the temperature is increased to at least −20° C. Optionally or additionally, the at least one equilibrating step is conducted when the temperature is increased to at least −10° C. Optionally or additionally, the at least one equilibrating step is conducted when the temperature is increased to at least 0° C. Optionally or additionally, the at least one equilibrating step is conducted when the temperature is increased to at least +10° C. Optionally or additionally, the at least one equilibrating step is conducted when the temperature is increased to at least +20° C. Optionally or additionally, the at least one equilibrating step is conducted when the temperature is increased to at least +30° C. Optionally or additionally, the at least one equilibrating step is conducted when the temperature is increased to at least +40° C.

Optionally, the dehydrating step (e) comprises six equilibrating steps, each equilibrating step being conducted when the temperature is increased by about 10° C. Further optionally, the dehydrating step (e) comprises six equilibrating steps, each equilibrating step being conducted when the temperature is increased to about −20° C., about −10° C., about 0° C., about +10° C., about +20° C., and about +30° C.

Optionally, the collagen source can be formed into collagen layers prior to the freezing step (d).

Optionally, the collagen dispersion can be filled into moulds to form collagen layers prior to the freezing step (d). Further optionally, the collagen dispersion can be filled into moulds to form collagen layers having an average thickness of 1-5 mm prior to the freezing step (d). Still further optionally, the collagen dispersion can be filled into moulds to form collagen layers having an average thickness of 1-3 mm prior to the freezing step (d). Still further optionally, the collagen dispersion can be filled into moulds having an average thickness of 1-5 mm and dimensions of 50×40 cm to form collagen layers prior to either or both of the freezing step (d) and the dehydrating step (e).

Optionally, the degrading step (f) comprises mechanically degrading the dehydrated collagen to a powder. Further optionally, the degrading step (f) is selected from milling, cutting, grinding, granulating, and a mixture thereof. Still further optionally, the degrading step (f) comprises milling the dehydrated collagen to a powder. Still further optionally, the degrading step (f) comprises milling the dehydrated collagen to a powder using a mesh size of 1 mm.

Optionally, the collagen powder is filled into a container.

Optionally, the collagen powder is sterilized. Further optionally, the collagen powder is sterilized after being filled into a container.

BRIEF DESCRIPTION OF THE DRAWINGS

Embodiments of the invention will now be described by way of non-limiting examples, and with reference to the accompanying drawings, in which.

EXAMPLES

Example 1

Manufacturing Process

Figure 1:
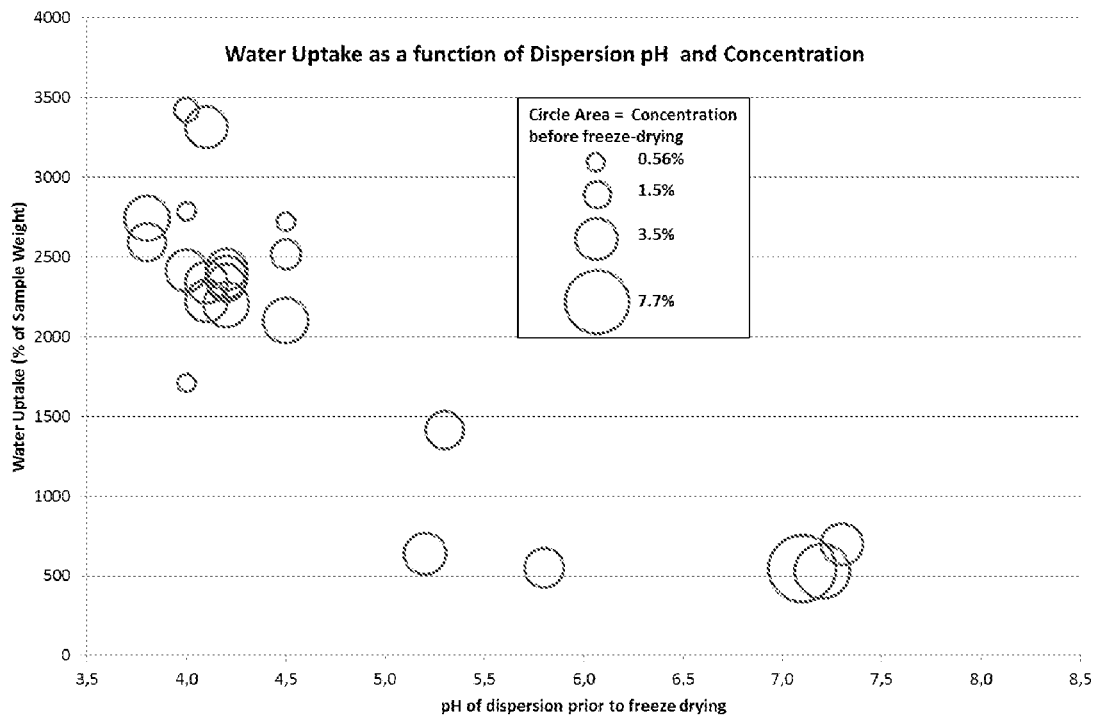
FIG. 1 is a graph illustrating water uptake of collagen powders prepared at different pH and collagen concentrations.

Collagen can be isolated from a number of sources, for example, animal hides and animal tendons. In a preferred embodiment, the collagen is isolated from animal tendon, for example equine or bovine tendon; although any known source of collagen, including fibrous tissue, optionally connective tissue, may be used and selected by one skilled in the art. Preferably, the collagen is isolated from equine tendon. In the method of isolation, equine tendons were milled to degrade the collagen source. The milled equine tendons were treated with a number of reagents, including 1N sodium hydroxide (NaOH) to remove microbiological contamination such as prions at the beginning of the process. Treatment steps with hydrogen peroxide and washing steps at different pH values were conducted, followed by a milling step, which was used to increase the surface for the next treatment step. The molecular weight of the collagen source was additionally reduced by treatment with the proteolytic enzyme pepsin at an approximate pH of 2.5. The pH was adjusted using an aqueous solution of 1N HCl. The pepsin was used to degrade contaminating serum components such as equine serum albumin (ESA) and resulted in the detachment of non-helical portions of the collagen molecule (telopeptides). During this process, the collagen material was also partially solubilised in the acidic medium. After filtration, the pH level was increased from 2.5 to 7.5 by addition of 1N sodium hydroxide (NaOH). This pH adjustment resulted in precipitation of the fibrillar collagen out of solution, which was then concentrated by means of centrifugation to provide a collagen dispersion having a concentration of about 3-30% (w/w). The resulting material was designated fresh collagen. The fresh collagen can be processed in several ways.

The fresh collagen can be packaged in suitable portions and frozen to −20° C. to be stored in a freezer until required for use. The resulting material was designated frozen collagen. The frozen collagen is thawed prior to use in the same manner as fresh collagen.

An amount of 63.3 g of frozen collagen source having an equivalent concentration of 28.4% dry content was thawed to room temperature and provided in a suitably sized stainless steel container. An amount of 20 g of 1N acetic acid was introduced to the collagen source to adjust the pH to 4.2. Purified water was introduced to the collagen dispersion to disperse the collagen source to a concentration of 1.5-4.0%.

After 5 minutes of soaking, a non-homogeneous semi-solid collagen dispersion was obtained and transferred into a cutting device (Heavy Duty Blender 39BL10, Waring Laboratory Services, Winsted, Conn., USA). The collagen dispersion was homogenized for a short period of time (5 seconds to 15 minutes) until a uniform semi-solid collagen dispersion with homogeneously hydrated and swollen collagen was obtained. The viscous collagen dispersion was weighed in amounts of 280 g onto suitable moulds or trays, for example stainless steel trays or large blister moulds with a size of 32×22 cm, and distributed to obtain a collagen layer having a thickness of 1-5 mm.

The distributed collagen dispersion was placed into a freeze dryer (Christ Epsilon 115), where it was first frozen and then dehydrated under vacuum by sublimation. The freezing and dehydrating conditions include chamber pressures between 50 and 500 μbar, and shelf temperatures that start at about −40° C. and are sequentially increased to +40° C. Typically, the freeze drying process (the freezing and dehydrating steps) has a total duration time of 18-30 hours. When the collagen is dehydrated, the freeze dryer chamber is brought to atmospheric pressure. The resultant collagen is in the form of collagen layers with slightly lower thickness than in the collagen dispersion layer (for example, the resultant collagen is in the form of collagen layers having a thickness of 1-4 mm).

The collagen layers were cut using scissors to units with dimensions that allow suitable feeding into a mill (Retsch ZM 100), for example layers having dimensions 1×1 cm, or 10×10 cm, depending on the milling equipment. For the Retsch ZM 100 mill, the collagen layers were cut using scissors to layers having dimensions 0.5×0.5 cm. The cut collagen layers were collected in a stainless steel container and milled, for example using an ultracentrifugal mill (Retsch ZM 100 at 18000 rpm at room temperature) with a mesh size of 1 mm using air cooling. The degraded collagen powder is collected and filled into polyethylene (polythene; PE) containers or bags for intermediary storage.

Subsequently, the collagen powder was aliquoted into final packaging configuration of 5 g per unit, optionally sterilized using ethylene oxide (EO) gas, and tested as described in Example 2.

Example 2

Analytical Characterization (Water Uptake)

Fluid absorption (water uptake) capacity of non-sterile collagen powder was tested by soaking a defined mass of 100-500 mg of collagen powder in purified water for a defined period of time (for example, 5 minutes); removing excess surface water by placing a sieve flat onto a tissue for 10 seconds and weighing the hydrated sample. The water uptake was analyzed under consideration of the pH and collagen concentration in the mixture prior to the freezing and dehydrating steps.

The pH of the collagen dispersion prior to the freezing and dehydrating steps strongly influenced the fluid absorption capacity. The water uptake is shown in FIG. 1 in dependence of pH of the collagen dispersion prior to the freezing and dehydrating steps. The concentration of the collagen dispersion is indicated by the area of the circles. The collagen powder prepared by the process of the present invention is shown at pH 3.5-5.0 and having collagen concentrations of 1.5-5.0%. Collagen powders having a lower collagen concentration exhibited comparable water uptake, but poor processing characteristics. The water uptake properties appear to be primarily defined by the pH; and a pH of <4.5 appears to provide a water absorption value of at least 20-fold greater than the sample weight.

A direct comparative test was conducted between a collagen powder prepared by the process according to the present invention, and sterile samples of two commercially available products. In each case, the water uptake was determined using the method described herein above.

A microfibrillar collagen hemostat (MCH), indicated for all surgical procedures including neurosurgery and urology, available from Davol, a Bard Company (RI, USA), and known as AVITENE™ Flour MCH; exhibited a water uptake of 6.5-fold greater than the sample weight tested.

A collagen powder made of sterile (gamma-irradiated), native, bioabsorbable bovine corium collagen, manufactured by Holphar Arzneimittel, von Fournier Pharma GmbH (Sulzbach, Germany) and known as PANGEN™ Puder exhibited a water uptake of 9.2-fold greater than the sample weight tested.

For both commercially-sourced products tested, the water uptake is significantly lower than for the collagen powder prepared according to the process of the present invention.

Example 3

Analytical Characterization (Bulk Density)

The bulk density of collagen powders was determined by filling a weighed amount of collagen powder (e.g. 1 g) into a graduated cylinder and determining the volume (e.g. 10-50 mL). The bulk density significantly increased with a higher collagen concentration in the collagen dispersion prior to the freezing and dehydrating steps.

Collagen powder prepared according to the process of the present invention exhibited bulk density values of 20-30 mg/cm$^3$ compared to collagen powders having a lower collagen concentration, which exhibited bulk density values of approximately 4 mg/cm$^3$.

Figure 2:
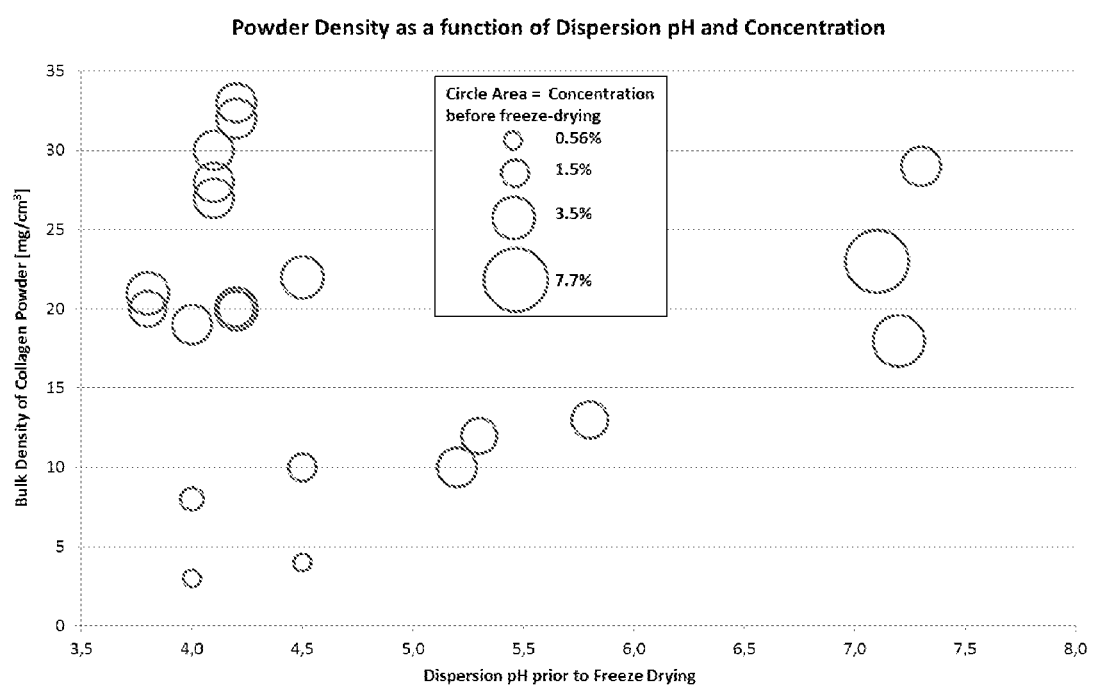
FIG. 2 is a graph illustrating bulk density of collagen powders prepared at different pH and collagen concentrations.

The relationship between the pH of the collagen dispersion, the concentration of the collagen dispersion; and the bulk density is shown in FIG. 2. The bulk density appears to be influenced by the collagen concentration.

The present invention therefore provides a collagen powder having an improved bulk density, improved processing characteristics, and increased fluid uptake.

The process of preparation according to the present invention also provides a preparation process having improved efficiency by removing the amount of water that needs to be removed during the preparation process (the amount of water that needs to be removed in the process of preparation according to the present invention is approximately 30-fold greater than the mass of collagen compared to 200-fold greater than the mass of collagen of known methods). This allows reduction of process time and increased throughput.

The invention claimed is:

1. A process for preparing a collagen powder, the process comprising the steps of:
   (a) providing a collagen source;
   (b) adjusting the collagen source to a collagen concentration of 1.5-4.0% (w/w) of the total weight of the collagen source and separately or simultaneously adjusting a pH of the collagen source to a pH of 3.5-5.0, to obtain a collagen dispersion;
   (c) disposing the collagen dispersion in a mold;
   (d) freezing the disposed collagen dispersion at a rate in a range from 0.3° C. per minute to 1.5° C. per minute to a temperature in a range from −33° C. to −42° C.;
   (e) dehydrating the frozen collagen; and
   (f) degrading the dehydrated collagen to a powder;
   wherein the collagen powder provides a water absorbency of at least 20-fold of its dehydrated weight.

2. The process according to claim 1, wherein the concentration-adjusting in step (b) is performed prior to the pH-adjusting in step (b).

3. The process according to claim 1, wherein the pH-adjusting in step (b) is performed prior to the concentration-adjusting in step (b).

4. The process according to claim 1, wherein the concentration-adjusting step (b) and the pH-adjusting step (b) are performed simultaneously.

5. The process according to claim 1, wherein the process comprises an additional step of mechanically degrading the collagen source prior to the freezing step (d) and after step (b).

6. The process according to claim 5, wherein the additional mechanical degrading step is conducted for a period of 5-900 seconds.

7. The process according to claim 1, wherein the collagen source is adjusted in step (b) to a collagen concentration equivalent of 1.5-4.0% (w/w) dehydrated collagen obtained in step (e).

8. The process according to claim 1, wherein the pH-adjusting in step (b) comprises introducing acetic acid to the collagen source.

9. The process according to claim 1, wherein the concentration-adjusting in step (b) and the pH-adjusting in step (b) are conducted simultaneously by introducing an acetic acid solution to the collagen source.

10. The process according to claim 1, wherein the concentration-adjusting in step (b) is conducted for a period of not less than 0.5 hours.

11. The process according to claim 1, wherein the pH-adjusting in step (b) is conducted for a period of 1-180 minutes.

12. The process according to claim 1, wherein the concentration-adjusting in step (b) and the pH-adjusting in step (b) are conducted simultaneously for a period of 1-180 minutes.

13. The process according to claim 1, wherein the dehydrating step (e) comprises removing an aqueous phase by reducing the pressure to a range of 0.05 to 1 mbar.

14. The process according to claim 1, wherein the dehydrating step (e) comprises increasing the temperature to +30° C. at a rate in a range from 0.3° C. to 1.5° C. per minute.

15. The process according to claim 1, wherein the dehydrating step (e) comprises increasing the temperature to +40° C. at a rate in a range from 0.3° C. to 1.5° C. per minute.

16. The process according to claim 1, wherein the dehydrating step (e) comprises at least one equilibrating step, and wherein the at least one equilibrating step comprises maintaining the temperature at a constant temperature, sufficient to allow the frozen collagen to reach a desired temperature.

17. The process according to claim 1, wherein the dehydrating step (e) comprises six equilibrating steps, each equilibrating step being conducted when the temperature is increased by 10° C.

18. The process according to claim 1, wherein the degrading step (f) comprises milling the dehydrated collagen to the powder using a mesh size of 1 mm.

19. The process according to claim 1, wherein the pH of the collagen source is adjusted to a pH of 3.5-4.5 in step (b).

20. A collagen powder obtained by the process of claim 1, wherein the collagen powder provides a water absorbency of at least 20-fold of its dehydrated weight and exhibits bulk density values of 20 to 30 mg/cm$^3$.

21. A process for preparing a collagen powder, the process comprising the steps of:
   (a) providing a collagen source;
   (b) adjusting the collagen source to a collagen concentration of 1.5-4.0% (w/w) of the total weight of the collagen source and to a pH of 3.5-5.0 to obtain a collagen dispersion;
   (c) freezing the collagen dispersion at a rate in a range from 0.3° C. per minute to 1.5° C. per minute to a temperature in a range from −33° C. to −42° C.;
   (d) dehydrating the frozen collagen; and
   (e) degrading the dehydrated collagen to a powder, wherein the collagen powder exhibits bulk density values of 20 to 30 mg/cm$^3$.

22. The process according to claim 21, wherein the collagen concentration is adjusted to 1.5-3.5% (w/w) of the total weight of the collagen source.

23. A process for preparing a collagen powder, the process comprising the steps of:
   (a) providing a collagen source;
   (b) adjusting the collagen source to a collagen concentration of 1.5-4.0% (w/w) of the total weight of the collagen source and a pH of 3.5-5.0 to obtain a collagen dispersion;
   (c) freezing the collagen dispersion at a rate in a range from 0.3° C. per minute to 1.5° C. per minute to a temperature in a range from −33° C. to −42° C.;
   (d) dehydrating the frozen collagen by removing water substance contained in the frozen collagen by increasing a temperature of the frozen collagen to at least +30° C. while under a pressure in a range from 0.05 mbar to 1 mbar; and
   (e) degrading the dehydrated collagen to a powder having a bulk density value in a range from 20 mg/cm$^3$ to 30 mg/cm$^3$.

24. The process of claim 23, wherein the dehydrating step (d) comprises at least one equilibrating step, and wherein the at least one equilibrating step comprises maintaining the temperature at a constant temperature, sufficient to allow the frozen collagen to reach a desired temperature.

25. The process of claim 24, wherein the at least one equilibrating step is conducted when the temperature is increased to at least −20° C.

26. A collagen powder having a bulk density value in a range from 20 mg/cm$^3$ to 30 mg/cm$^3$ and a water absorbency of at least 20-fold of its dehydrated weight.

* * * * *